(12) United States Patent
Schlomka (10) Patent No.: US 7,587,021 B2
(45) Date of Patent: Sep. 8, 2009

(54) COMPUTER TOMOGRAPHY APPARATUS

(75) Inventor: Jens-Peter Schlomka, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 11/813,126

(22) PCT Filed: Jan. 10, 2006

(86) PCT No.: PCT/IB2006/050094

§ 371 (c)(1),
(2), (4) Date: Jun. 29, 2007

(87) PCT Pub. No.: WO2006/075295

PCT Pub. Date: Jul. 20, 2006

(65) Prior Publication Data

US 2008/0112532 A1 May 15, 2008

(30) Foreign Application Priority Data

Jan. 12, 2005 (GB) ................. 0500535.0

(51) Int. Cl.
*G01N 23/04* (2006.01)
*G01N 23/20* (2006.01)
(52) U.S. Cl. ............................. 378/6; 378/87
(58) Field of Classification Search .............. 378/4–6, 378/86–89
See application file for complete search history.

(56) References Cited

U.S. PATENT DOCUMENTS

| 4,754,469 A | 6/1988 | Harding et al. |
| 4,887,285 A | 12/1989 | Harding et al. |
| 4,963,746 A | 10/1990 | Morgan et al. |
| 5,265,144 A | 11/1993 | Harding et al. |
| 6,721,387 B1 | 4/2004 | Naidu et al. |
| 6,744,845 B2 | 6/2004 | Harding et al. |
| 6,950,493 B2 * | 9/2005 | Besson ................ 378/16 |
| 2002/0131549 A1 | 9/2002 | Oikawa |
| 2004/0264628 A1 | 12/2004 | Besson |

FOREIGN PATENT DOCUMENTS

| DE | 10009285 A1 | 8/2001 |
| JP | 09187450 A | 7/1997 |
| JP | 2001120539 A | 5/2001 |
| WO | WO2004044848 A1 | 5/2004 |
| WO | WO2004105610 A1 | 12/2004 |

OTHER PUBLICATIONS

Schneider et al: "Coherent Scatter Computed Tomography Applying a Fan-Beam Geometry"; Proceedings of the SPIE, SPIE, vol. 4320, Feb. 18, 2001,XP008004551.
Castro et al: "Coherent Scattering X-Ray Imaging at the Brazilian National Synchrotron Laboratory: Preliminary Breast Images"; Nuclear Instruments & Methods in Physics Research, Section-A: Accelerators, Spectrometer, Detectors and Associated Equipment, Elsevier Publishers, vol. 548, No. 1-2, Aug. 11, 2005, pp. 116-122. XP005027425.

\* cited by examiner

*Primary Examiner*—Edward J Glick
*Assistant Examiner*—Thomas R Artman (57) ABSTRACT

A computer tomography apparatus for examination of an object of interest includes detecting elements adapted to detect electromagnetic radiation scattered from the object of interest in an energy-resolving manner. A combination unit is adapted to combine signals detected by different detecting elements such as to reduce the amount of data to be processed for determining structural information concerning the object of interest.

19 Claims, 4 Drawing Sheets

COMPUTER TOMOGRAPHY APPARATUS

The invention relates to the field of X-ray imaging. In particular, the invention relates to a computer tomography apparatus, to a method of examining an object of interest with a computer tomography apparatus, to a computer-readable medium and to a program element.

Over the past several years, X-ray baggage inspections have evolved from simple X-ray imaging systems that were completely dependent on an interaction by an operator to more sophisticated automatic systems that can automatically recognize certain types of materials and trigger an alarm in the presence of dangerous materials. An inspection system has employed an X-ray radiation source for emitting X-rays which are transmitted through or scattered from the examined package to a detector.

Computed tomography (CT) is a process of using digital processing to generate a three-dimensional image of the internals of an object from a series of two-dimensional X-ray images taken around a single axis of rotation. The reconstruction of CT images can be done by applying appropriate algorithms.

An imaging technique based on coherently scattered X-ray photons or quanta is the so-called "coherent scatter computer tomography" (CSCT). CSCT is a technique that produces images of (particularly the low angle) scatter properties of an object of interest. These depend on the molecular structure of the object, making it possible to produce material-specific maps of each component. The dominant component of low angle scatter is coherent scatter. Since coherent scatter spectra depend on the atomic arrangement of the scattering sample, coherent scatter computer tomography (CSCT) is a sensitive technique for imaging spatial variations in the molecular structure of baggage or of biological tissue across a two-dimensional object section. In other words, CSCT reconstructs an image taking into account information contained in coherently scattered radiation.

DE 100 09 285 A1 discloses the principle of an imaging method based on coherently scattered X-ray radiation. For this purpose, a small fan-beam of radiation with a small divergence out of the fan-plane is guided to the object. Then, the transmitted radiation is measured as well as the radiation which is scattered by the object out of the plane of the fan.

The imaging technique based on coherently scattered X-ray photons named coherent scatter computer tomography (CSCT) may use a fan-shape primary beam combined with two dimensional detectors, so that the transmission tomography and scatter tomography can be measured simultaneously.

However, a large amount of data has to be processed in order to reconstruct an image of an object of interest from measured detecting signals with high quality.

It would be desirable to have a computer tomography apparatus allowing a sufficiently fast processing of data for image reconstruction.

This can be achieved by providing a computer tomography apparatus, a method of examining an object of interest with a computer tomography apparatus, a computer-readable medium and a program element according to the independent claims.

The computer tomography apparatus for examination of an object of interest comprises detecting elements adapted to detect, as detecting signals, electromagnetic radiation scattered from an object of interest in an energy-resolving manner. Further, a combination unit is provided which is adapted to combine detecting signals detected by different detecting elements such as to reduce the amount of data to be processed for determining structural information concerning the object of interest.

Moreover, the invention provides a method of examining an object of interest with a computer tomography apparatus, comprising the steps of detecting, as detecting signals, electromagnetic radiation scattered from an object of interest in an energy-resolving manner, and combining different detecting signals such as to reduce the amount of data to be processed for determining structural information concerning the object of interest.

Beyond this, a computer-readable medium is provided, in which a computer program of examining an object of interest with a computer tomography apparatus is stored which, when being executed by a processor, is adapted to carry out the above-mentioned method steps.

Moreover, a program element of examining an object of interest is provided, which, when being executed by a processor, is adapted to carry out the above-mentioned method steps.

The examination of an object of interest according to the invention can be realized by a computer program, i.e. by software, or by using one or more special electronic optimization circuits, i.e. in hardware, or in hybrid form, i.e. by means of software components and hardware components.

The characterizing features of the invention particularly have the advantage that a pre-processing of a set of measured data is carried out prior to reconstructing a three-dimensional image from energy-resolving detecting signals by combining or grouping detecting signals which have been detected by different detecting elements. Particularly, detecting signals can be pooled in order to at least partially remove some redundancy of the signals and of their information content. In other words, different signals yielding the same information, similar information or complementary information may be combined to a single signal so that, by grouping the measured detecting signals, a reduction of the amount of data to be processed subsequently and an improvement of the statistical meaningfulness of this data can be achieved.

With energy-resolving detectors being implemented in the CSCT system of the invention, the information of the detecting signals can be used efficiently to obtain a very high image quality. By grouping detecting signals received by different detecting elements, maximum information can be derived from a measurement with low computational burden, and thus the speed and the accuracy of a computer tomography analysis is significantly increased.

Particularly, the invention teaches to pre-process captured data for multi-line energy-resolved coherent scatter computer tomography (CSCT). The invention may be implemented advantageously for instance in the fields of baggage inspection or medical diagnosis.

According to one aspect of the invention, the pre-processing for a multi-line energy-resolved CSCT technology involves pre-processing of X-ray signals in rows or columns in a two-dimensional energy-resolved detector leading to an improved data rate for image reconstruction of computed tomography signals.

One idea of the invention is that it deals with CSCT and combines scattered data of a multi-line detector. The pre-processing is done in a sophisticated way such that the data are sorted regarding their wave vector transfer parameter. Thus, one dimension of data can be eliminated in reconstruction, yielding an increased velocity of data processing and image reconstruction: When two-dimensional energy-resolving detectors are used, a three-dimensional data set is acquired for each projection, namely the two-dimensional detector coordinates and the one-dimensional energy distribution. This results in a rather high data rate from a gantry. For reconstruction, one dimension can be eliminated by the invention. Consequently, an efficient reduction of the data rate which is used for further processing and reconstruction is obtained. The invention describes such an elimination process, which is carried out preferably during a pre-processing procedure. If this elimination by combining is carried out on the gantry, the data rate can be reduced by a factor equivalent to the number of detector rows (for instance 5 to 20).

A procedure for such a pre-processing of energy-resolved multi-line CSCT data may include, according to an embodiment, that the output of each detector pixel is corrected for sensitivity fluctuations and energy scale variation and is normalized to the primary beam. Other pixel-wise pre-processing steps may be carried out additionally at this position of the analysis process. In a subsequent step, the energy scales of all channels (preferably except the reference channel) may be multiplied with an adjustment factor which may be denoted as $f_i$. Usable energy regions (regions of interest) can be selected for each individual detector line. Then all data may be added for further processing.

Next, preferred embodiments of the computer tomography apparatus will be described. These embodiments may also be applied for the method of examining an object of interest, for the computer-readable medium and for the program element.

The combination unit may be adapted to combine detecting signals detected by different detecting elements based on a position and an energy of the detecting signals. Thus, the parameters/criteria of the position of a detecting element on a detector array and the estimated energy of the detected radiation are appropriate parameters which may be taken as a reliable basis for deciding which signals are to be combined, since—taken alone—they introduce some redundancy which can be reduced according to the invention by combining these signals. For instance, signals having different energies and having different positions may be combined in case that a special condition is fulfilled for the energy and position parameters. For instance, signals may be combined for which the product of photon energy and angular distance of the detection element detecting this photon from radiation transmitted through the object under investigation is constant.

The detecting elements may be grouped to form groups of detecting elements, wherein each group may be arranged to detect electromagnetic radiation scattered to a respective distance from a group of detecting elements detecting electromagnetic radiation beam transmitted (and not deflected by being scattered) through the object of interest. This grouping allows to pool different signals in a manner to reduce the data amount to be processed during the subsequent reconstruction of a three-dimensional image.

The combination unit may be adapted to combine detecting signals with an essentially equal product of energy of the detected electromagnetic radiation and the distance from unscattered radiation as defined above. As will be described below referring to FIG. 3, this product is an appropriate criteria for combining signals.

The combination unit may further be adapted to combine detecting signals with an essentially equal wave vector transfer of coherently scattered electromagnetic radiation to an object of interest. Such detecting signals show some redundancy and may improve the statistics of the analysis when being evaluated group-wise.

Further, the computer tomography apparatus may comprise a rotatable gantry, wherein the combination unit may be arranged on the gantry. By carrying out the pre-processing method already on the gantry before transferring the signals for a further analysis to a determination unit, only a very small amount of signals has to be transferred, which increases the velocity of processing. The transfer of detected data from the rotating gantry to a non-rotating determination unit (for the sake of further processing of the data) can be performed via a data transmission channel. This transfer can be done via a direct (mechanical) electric connection (e.g. by a collector ring, also denoted as "Schleifring") or in a contactless manner, particularly by transmitting electromagnetic radiation (e.g. by an optical transmission or an RF transmission). By reducing the amount of data to be transmitted from the rotating gantry to a static determination unit, the bandwidth needed for the data transmission channel is significantly reduced.

The computer tomography apparatus may comprise a correction unit adapted to correct the detecting signals before combining the detecting signals. Such an early correction of the signals, before further processing, increases the reliability and the quality of a reconstructed image, since artifacts can be removed from the spectrum by the correction.

For instance, the correction unit may be adapted to correct the detecting signals with respect to sensitivity fluctuations and/or with respect to energy scale fluctuations. Particularly, the pre-processing may include the consideration of an energy-dependence of an acceptance of the detecting elements. This allows a subsequent reconstruction of the image of the object of interest with increased accuracy, since it refines the used model.

Further, a normalizing unit may be provided adapted to normalize the detecting signals before combining the detecting signals. Such a normalization further increases the reliability and reproducibility of the results.

The computer tomography apparatus may comprise an attenuation correction unit adapted to correct influences of attenuation of the detecting signals before combining the detecting signals. Such an attenuation correction improves the quality of the reconstructed image.

Moreover, the computer tomography apparatus may comprise a determination unit adapted to determine structural information concerning the object of interest based on an analysis of the combined detecting signals. Thus, after having pre-processed the detecting signals by grouping them in order to reduce the data rate to be processed, these pre-processed signals may be provided to the determination unit which then carries out a three-dimensional reconstruction to obtain information concerning the object of interest.

The computer tomography apparatus may further comprise a selection unit adapted to select for (all or for a part of) the groups of detecting elements a respective range of energy of detecting signals which are provided to the determination unit. Thus, for each detecting element or for detecting element of a group (for instance a row or a column of detecting elements), a particular region of interest of energies of scattered electromagnetic radiation can be defined to increase the meaningfulness of the reconstruction of the three-dimensional image. For instance, for large scatter angles, only signals having energies below a respective threshold value may be selected for further analysis, and for smaller scatter angles only signals having energies above a respective threshold value may be selected for further analysis.

The computer tomography apparatus may further comprise an electromagnetic radiation source (like an X-ray source) adapted to emit electromagnetic radiation to an object of interest, and may comprise a collimator arranged between the electromagnetic radiation source and the detecting elements, the collimator being adapted to collimate an electromagnetic radiation beam emitted from the electromagnetic radiation source. Particularly, a primary beam of fan-beam geometry can be used.

The computer tomography apparatus of the invention may be adapted as a coherent scatter computer tomography apparatus (CSCT), i.e. the computer tomography apparatus may be configured and operated according to the CSCT technology described above.

The detecting elements of the computer tomography apparatus may form a multi-line detector array. For instance, the detecting elements may form a two-dimensional detector array. By using a multi-slice detector array, a very high resolution may be achieved, and a high number of signals can be captured simultaneously.

The computer tomography apparatus may be arranged such that the detecting elements form a matrix-like detector array having a plurality of rows (or lines) and having a plurality of columns of detecting elements. In such a matrix-like detector array (which may be realized as a two-dimensional detector), the combination unit may be adapted to combine detecting signals detected by different detecting elements of a column. In other words, detecting signals of all detecting elements related to a particular column of such a matrix-like detector array may be combined to reduce redundancy. Particularly, if a predefined correlation (see for instance equation (4) and corresponding description) between the position and the energy of photons impinging on different pixels of a column of the matrix is fulfilled, then these signals may be combined/added. Thus, the amount of data to be processed subsequently, is significantly increased.

The computer tomography apparatus according to the invention may be configured as one of the group consisting of a baggage inspection apparatus, a medical application apparatus, a material testing apparatus and a material science analysis apparatus. A preferred field of application of the invention is baggage inspection, since the defined functionality of the invention allows a secure and reliable analysis of the content of a baggage item which enables one to detect suspicious content, even allowing to determine the type of material inside such a baggage item. The invention creates a high quality automatic system that can automatically recognize certain types of material and, if desired, trigger an alarm in the presence of dangerous material. Such an inspection system may have employed the computer tomography apparatus of the invention with an X-ray radiation source for emitting X-rays which are transmitted through or scattered from the examined package to a detector allowing to detect coherently scattered radiation in an energy-resolved manner.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

The illustration in the drawings is schematically

In the following, referring to FIG. 1, a computer tomography apparatus 100 will be described having implemented energy-resolved CSCT.

The CSCT computer tomography apparatus 100 has an X-ray source 101 for emitting an X-ray beam which is guided through a slit collimator 102 to form a primary fan-beam 104 impinging an object to be located in an object region 103. A multi-line detector is constituted by a central detection element 105 (i.e. a central row for the detection of X-rays of the fan-beam transmitted through an object) and by a plurality of energy-resolving detection elements 106 (i.e. a plurality of energy-resolving detector lines).

Thus, a central detector (single-line or multi line) is provided to detect directly transmitted radiation. A detector placed off-set is energy-resolving and measures scattered radiation. With this method and apparatus, a proper spectral resolution can be achieved also with polychromatic primary radiation.

Figure 1:
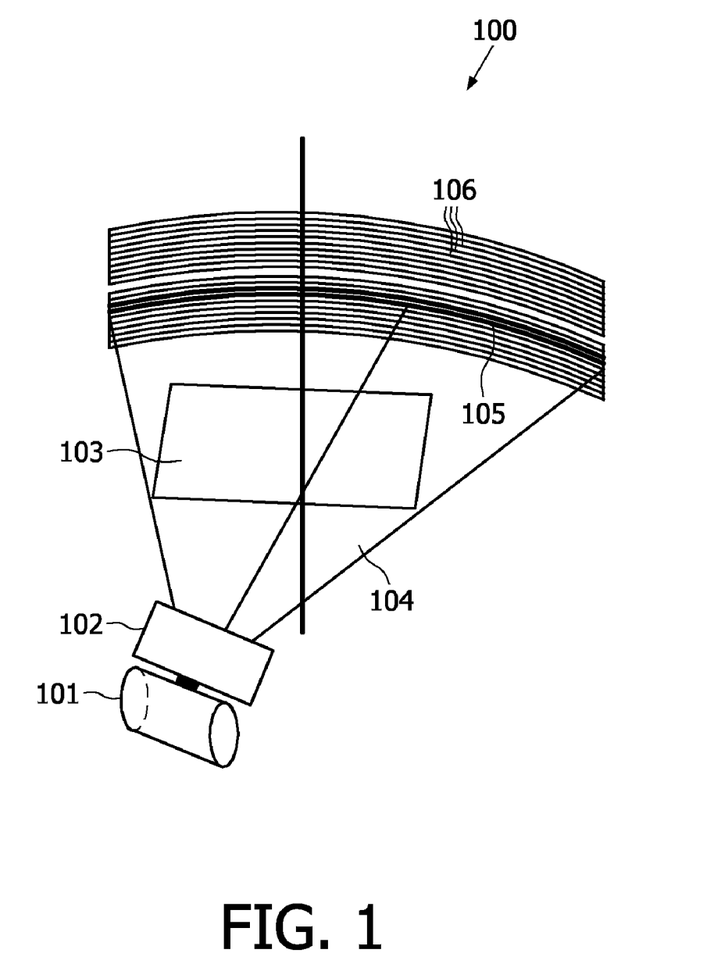
FIG. 1 shows a computer tomography apparatus including energy-resolved CSCT.

Thus, FIG. 1 shows a geometry for energy-resolved CSCT. The central detection line 105 measures transmitted radiation, whereas the one or more detection lines 106 are configured to perform an energy-resolving measurement. However, with the apparatus 100 shown in FIG. 1, a complicated analysis of the signals is necessary, since the apparatus 100 produces a huge amount of data to be processed.

Figure 2:
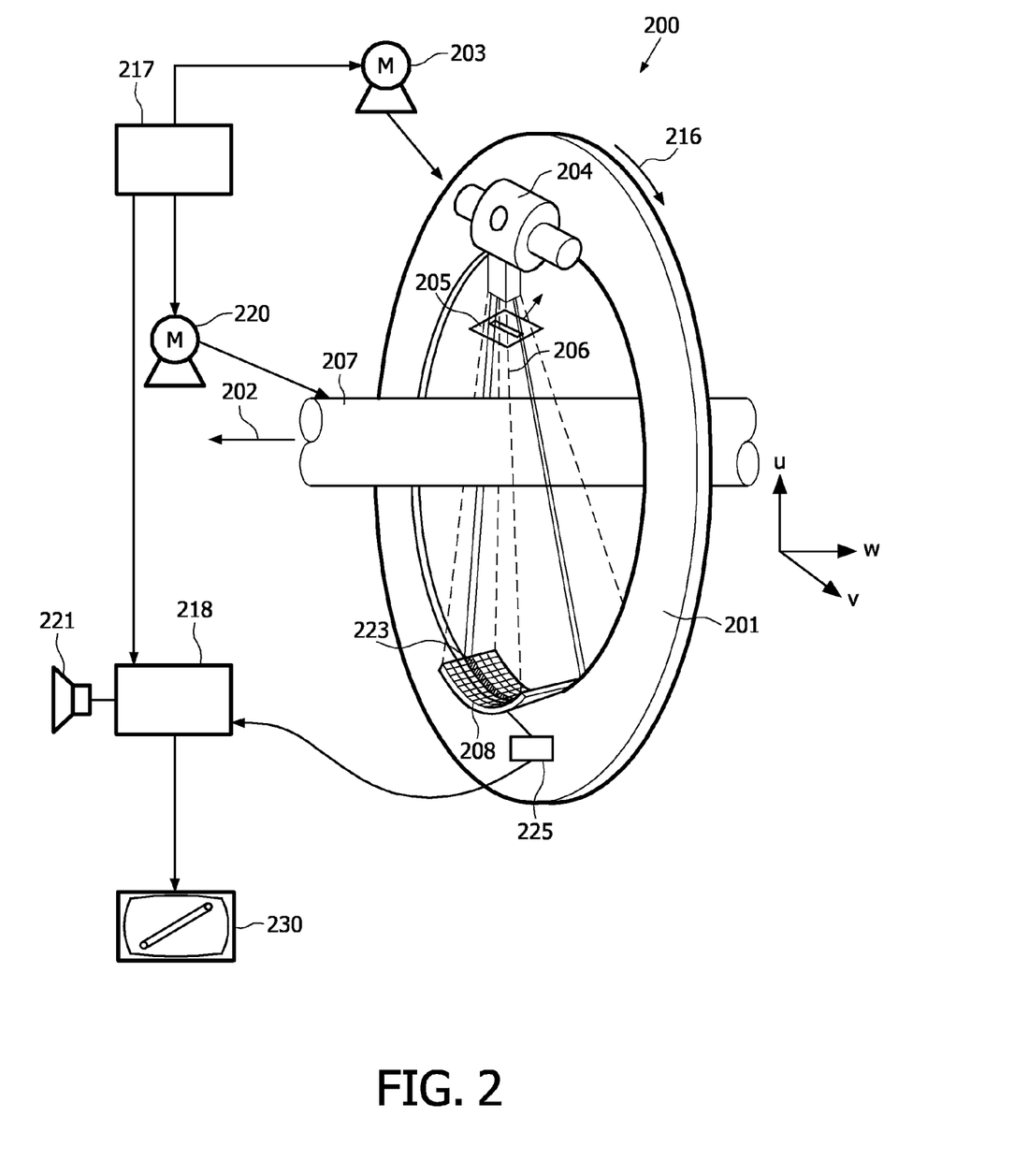
FIG. 2 shows a computer tomography apparatus according to a first embodiment of the invention.

FIG. 2 shows an exemplary embodiment of a CSCT (coherent scatter computed tomography) scanner system 200 according to the present invention.

With reference to this exemplary embodiment, the present invention will be described for the application in baggage inspection to detect hazardous materials, such as explosives, in items of baggage. However, it should be noted that the present invention is not limited to this application, but may also be applied in the field of medical imaging, or other industrial applications such as material testing.

The computer tomography apparatus 200 depicted in FIG. 2 is a fan-beam CT scanner. The scanner depicted in FIG. 2 comprises a gantry 201, which is rotatable around a rotational axis 202. The gantry 201 is driven by means of a motor 203. Reference numeral 204 designates a source of radiation such as an X-ray source, which, according to an aspect of the present invention, emits a polychromatic radiation.

Reference numeral 205 designates an aperture system which forms the radiation beam emitted from the radiation source to a fan-shaped radiation beam 206. The fan-beam 206 is directed such that it penetrates an object of interest 207 arranged in the center of the gantry 201, i.e. in an examination region of the CSCT scanner, and impinges onto the detector 208. As may be taken from FIG. 2, the detector 208 is arranged on the gantry 201 opposite to the source of radiation 204, such that the surface of the detector 208 is covered by the fan-beam 206. The detector 208 depicted in FIG. 2 comprises a plurality of detector elements 223 each capable of detecting, in an energy-resolving manner, X-rays which have been coherently scattered by the object of interest 207.

During a scan of the object of interest 207, the source of radiation 204, the aperture system 205 and the detector 208 are rotated along the gantry 201 in the direction indicated by an arrow 216. For rotation of the gantry 201 with the source of radiation 204, the aperture system 205 and the detector 208, the motor 203 is connected to a motor control unit 217, which is connected to a calculation or determination unit 218.

In FIG. 2, the object of interest 207 is an item of baggage which is disposed on a conveyor belt (not shown). During the scan of the object of interest 207, while the gantry 201 rotates around the item of baggage 207, the conveyor belt displaces the object of interest 207 along a direction parallel to the rotational axis 202 of the gantry 201. By this, the object of interest 207 is scanned along a helical scan path. The conveyor belt may also be stopped during the scans to thereby measure signal slices. Instead of providing a conveyor belt, for example in medical applications where the object of interest 207 is a patient, a moveable table is used. However, it should be noted that in all of the described cases it is also possible to perform a circular scan, where there is no displacement in a direction parallel to the rotational axis 202, but only the rotation of the gantry 201 around the rotational axis 202.

As shown in FIG. 2, the invention can be realized by a fan-beam configuration. In order to generate a primary fan-beam, the aperture system 205 is configured as a slit collimator.

The detector 208 is connected to the determination unit 218. The determination unit 218 receives the detection result, i.e. the read-outs from the detector elements 223 of the detector 208 after a pre-processing by a combination unit 225 and determines a scanning result on the basis of these read-outs. Furthermore, the determination unit 218 communicates with the motor control unit 217 in order to coordinate the movement of the gantry 201 with motors 203 and 220 with the conveyor belt.

The determination unit 218 may be adapted for reconstructing an image from read-outs of the detector 208 using a tomographic reconstruction. A reconstructed image generated by the calculation unit 218 may be output to a display 230.

The determination unit 218 may be realized by a data processor to process read-outs from the detector elements 223 of the detector 208.

Furthermore, as may be taken from FIG. 2, the determination unit 218 may be connected to a loudspeaker 221, for example to automatically output an alarm in case of the detection of suspicious material in the item of baggage 207.

The computer tomography apparatus 200 is thus adapted to examine an object of interest 207 and comprises the detecting elements 223 to detect, as detecting signals, electromagnetic radiation coherently scattered from the object of interest 207 in an energy-resolving manner. The combination unit 225 is coupled to an output of the detecting elements 223 and is adapted to combine detecting elements detected by different detecting elements 223 such as to reduce the amount of data to be processed by the determination unit 218 for determining structural information concerning the object of interest 207.

The combination unit 225 is adapted to combine detecting signals detected by different detecting elements 223 based on a position of the detection signal on the essentially two-dimensional detection array 208 and based on an energy of the detecting signals. Particularly, the detecting elements 223 are grouped to form groups of detecting elements 223, wherein each group is arranged to detect electromagnetic radiation scattered to a respective distance with respect to a central detecting element line detecting radiation transmitted through the object of interest 207.

As will be described in more detail referring to FIG. 3, the combination unit 225 combines detecting signals with an essentially equal product of the energy of the detected electromagnetic radiation and the distance of a detecting element 223 with respect to a central detecting element line 105. The combination unit 225 combines detecting signals with an essentially equal wave vector transfer of coherently scattered electromagnetic radiation to the object of interest 207. As can be seen from FIG. 2, the combination unit 225 is arranged and fixed on the rotatable gantry 201.

The determination unit 218 is coupled with an output of the combination unit 225 so that the combination unit 225 provides the determination unit with the reduced amount of data which have been pre-processed by the combination unit 225. The determination unit 218 is adapted to determine structural information concerning the object of interest 207 based on an analysis of the combined detecting signals.

The electromagnetic radiation source 204 is adapted to emit electromagnetic radiation to the object of interest 207 and comprises a collimator 205 arranged between the electromagnetic radiation source 204 and the detecting elements 223. The collimator is shaped to collimate an electromagnetic radiation beam emitted by the electromagnetic radiation source 204 to form a fan-beam.

Since the object of interest 207 is an item of baggage, the computer tomography apparatus is configured as a baggage inspection apparatus.

In the following, referring to FIG. 3, the way how different signals are combined according to an embodiment of the invention will be described in more detail.

When a plurality of energy-resolving detector rows 302 are used (see FIG. 2 and FIG. 3), the data set received has a partial redundancy. This means that different detector rows 302 may cover overlapping regions of wave vectors. This is used to improve the statistics and thus to reduce the necessary measurement time. In the following, referring to FIG. 3, it will be described how the data may be pre-processed for this purpose.

The structure factor being the fingerprint of the material of an object of interest 207 at which electromagnetic radiation is scattered can be formulated in dependence of the wave vector transfer x. It depends on the energy of the photon E and on the scatter angle $\Theta$, as can be seen in FIG. 3:

$$x = (|k_f - k_i|)/4 = \frac{E}{hc}\sin(\Theta/2) = \frac{1}{\lambda}\cdot\sin(\Theta/2) \tag{1}$$

$k_f$ denotes the final and $k_i$ denotes the initial wave vector of the radiation. The Planck number is denoted as h, c is the velocity of light, and $\lambda$ is the wavelength of the radiation.

Figure 3:
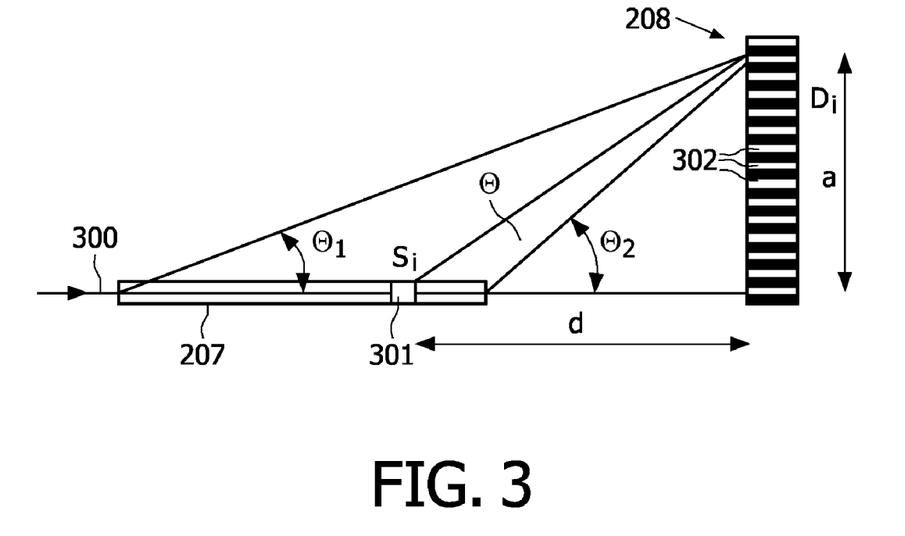
FIG. 3 shows a model geometry for the scattering process in the case of a computer tomography apparatus of the invention.

The parameters of equation (1) can be seen in FIG. 3. FIG. 3 is a side view of the scattering geometry (wherein the said direction is enlarged for a better illustration). The incoming radiation 300 is scattered on an object slice 301 of the object of interest 207 out of the fan-beam plane and impinges onto the detector 208. Different detector rows 302 are shown each comprising a plurality of the detecting elements 223. Photons that reach one particular detector element 223 related to a detecting row 302 were scattered on a different angles $\Theta$ depending on the position of the scatter event inside the object of interest 207, namely depending on the object slice 301 at which the photon has been scattered.

Thus, FIG. 3 shows the scatter geometry in a CSCT constitution. A detector element $D_i$ of a multi-line detector 208 is located at a distance a from the primary beam. Then, for an object point $S_i$, a distance d from the detector 208 is correlated with a scatter angle $\Theta$:

$$\Theta = a\tan(a/d) \tag{2}$$

For not too large angles, equation (2) can be rewritten in good approximation:

$$\Theta \approx \frac{a}{d}, x \approx \frac{E}{hc} \cdot \frac{a}{2d} \quad (3)$$

Thus, x is proportional to the distance of the detector from the primary beam a and is proportional to the energy E.

A scatter peak from an object having a fixed wave vector transfer $x_0$ appears in different detector rows 302 at different energies $E_i$, wherein the product $E_i \, a_i$ is constant:

$$x_0 = \frac{E_i}{hc} \cdot \frac{a_i}{2d} \quad (4)$$

Figure 4:
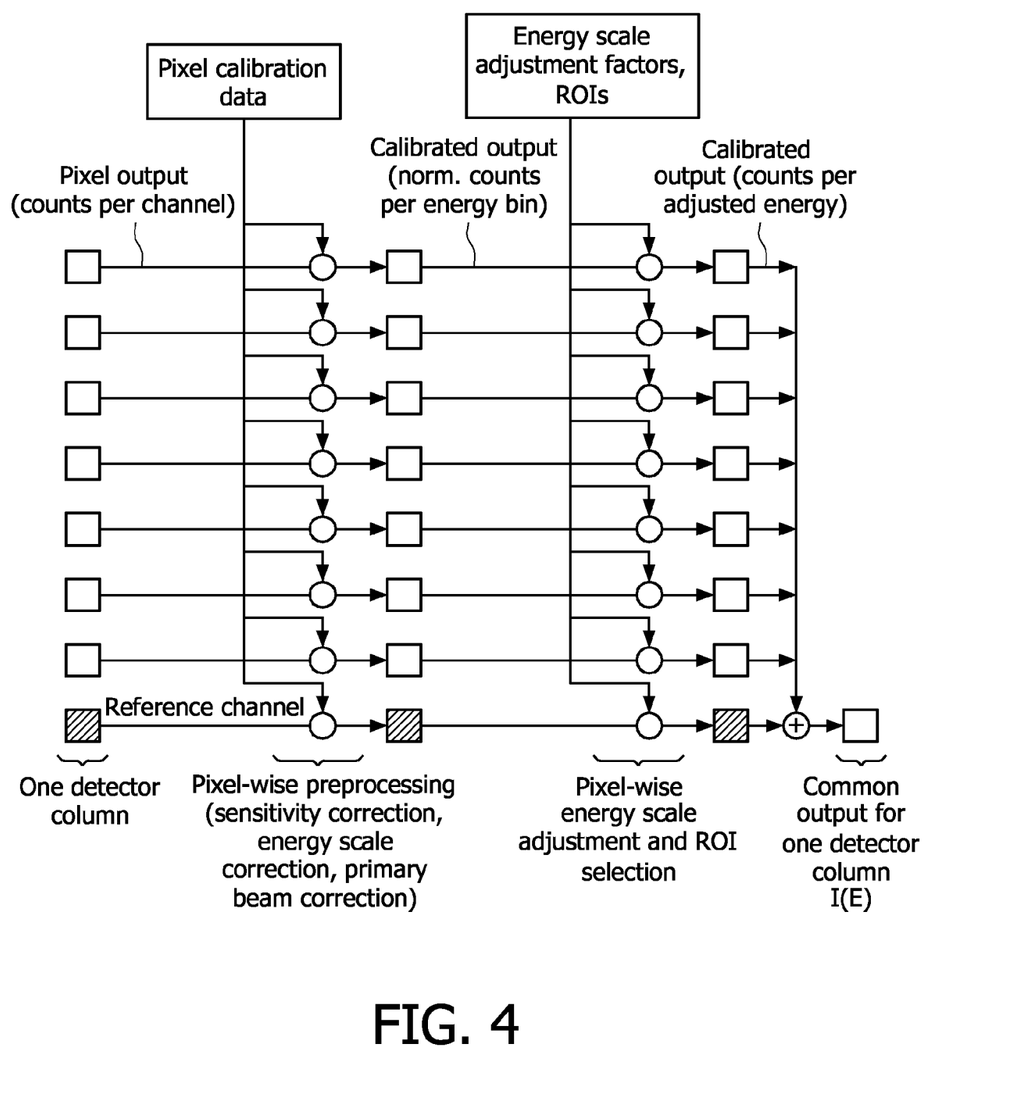
FIG. 4 shows a diagram illustrating a concept of the invention.

Using the relation of equation (4), data of different detector rows 302 can now be combined, as shown in FIG. 4.

Some pre-processing steps are to be carried out prior to the data combination (in a pixel-wise manner), namely a sensitivity correction, an energy scale calibration, a primary beam correction, etc.

Further, a reference row may be defined which is located at a distance $a_0$ from the primary beam. The energy scale of this reference line is used as a basis.

Subsequently, the energy scale of the other detector lines located at a distance $a_i$ ($a_i \neq a_0$) from the primary beam are multiplied with a correction factor $f_i = a_i/a_0$, i.e. for a smaller distance from the primary beam the measured energy scale is compressed, and vice versa. This ensures that a scatter peak appears at the same "adjusted energy", independently of the detector row 302.

Energy regions (regions of interest) can be chosen which shall be further processed. Only these parts of the spectra are further processed. For instance, at large scatter angles, only the small energies can be taken into account, and at smaller scatter angles, only the larger energies can be taken into account.

Then, the counting rates of the different detector rows may be added.

Such a pre-processing can be carried out already on the gantry 201. This has the advantage that, per projection, only a data set of the dimension given by the product between the number of energy channels and the number of detector columns has to be transferred to the determination unit 218. The original data set has an amount of data given by the product of the number of energy channels, of the number of detector columns and of the number of detector rows, i.e. a reduction of the factor which is given by the number of detector rows has been achieved.

FIG. 4 shows an example for the procedure for the pre-processing of energy-resolved multi-line CSCT data: The output of each pixel is corrected for sensitivity fluctuations, energy scale variations and normalized to the primary beam. Other pixel-wise pre-processing is carried out at this position. In a next step, the energy scales of all channels except the reference channels are multiplied with adjustment factor $f_i$. Usable energy regions (ROIs) can be selected for each individual detector line. Then all data are added for further processing.

Figure 5:
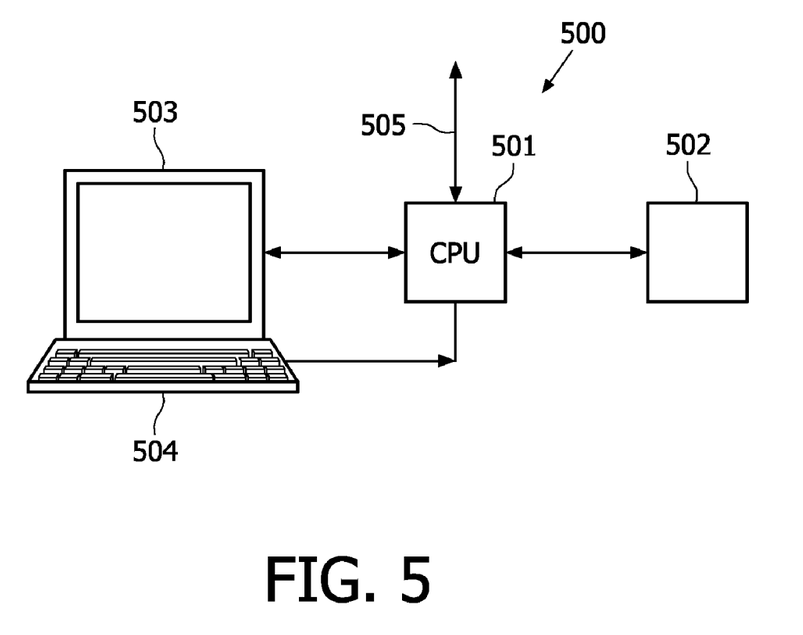
FIG. 5 shows an exemplary embodiment of a data processing device to be implemented in the computer tomography apparatus of the invention.

FIG. 5 depicts an exemplary embodiment of a data processing device 500 according to the present invention for executing an exemplary embodiment of a method in accordance with the present invention. The data processing device 500 depicted in FIG. 5 comprises a central processing unit (CPU) or image processor 501 connected to a memory 502 for storing an image depicting an object of interest, such as a patient or an item of baggage. The data processor 501 may be connected to a plurality of input/output network or diagnosis devices, such as an MR device or a CT device. The data processor 501 may furthermore be connected to a display device 503, for example a computer monitor, for displaying information or an image computed or adapted in the data processor 501. An operator or user may interact with the data processor 501 via a keyboard 504 and/or other output devices, which are not depicted in FIG. 5. Furthermore, via the bus system 505, it is also possible to connect the image processing and control processor 501 to, for example a motion monitor, which monitors a motion of the object of interest. In case, for example, a lung of a patient is imaged, the motion sensor may be an exhalation sensor. In case the heart is imaged, the motion sensor may be an electrocardiogram (ECG).

Exemplary technical fields, in which the present invention may be applied advantageously, include baggage inspection, medical applications, material testing, and material science. An improved image quality and a reduced amount of calculations in combination with a low effort may be achieved. Also, the invention can be applied in the field of heart scanning to detect heart diseases.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. A computer tomography apparatus for examination of an object of interest, the computer tomography apparatus comprising:
    an electromagnetic radiation source adapted to emit primary electromagnetic radiation to the object of interest;
    detecting elements adapted to detect electromagnetic radiation scattered from the object of interest in an energy resolving manner; and
    a combination unit adapted to combine detecting signals detected by different detecting elements thereby reducing the amount of data to be processed for determining structural information concerning the object of interest;
    wherein the combination unit is adapted to combine signals with an essentially equal product of energy of the detected electromagnetic radiation and a distance of the detected electromagnetic radiation from the primary electromagnetic radiation detected by a detecting element, including signals having different energies and different distances.

2. The computer tomography apparatus according to claim 1, wherein the combination unit is adapted to combine detecting signals detected by different detecting elements based on a position and an energy of the detecting signals.

3. The computer tomography apparatus according to claim 1, wherein the detecting elements are grouped to form groups of detecting elements, each group being arranged to detect electromagnetic radiation scattered to a respective distance from a group of detecting elements detecting electromagnetic radiation being transmitted through the object of interest.

4. The computer tomography apparatus according to claim 3, further comprising:
    a determination unit adapted to determine structural information concerning the object of interest based on an analysis of the combined detecting signals; and
    a selection unit adapted to select, for at least a part of the groups of detecting elements, a respective range of energy of detecting signals which are provided to the determination unit.

5. The computer tomography apparatus according to claim 1, wherein the combination unit is adapted to combine detecting signals with an essentially equal wave vector transfer of coherently scattered electromagnetic radiation to an object of interest.

6. The computer tomography apparatus according to claim 1, comprising a rotatable gantry, wherein the combination unit is arranged on the gantry.

7. The computer tomography apparatus according to claim 1, comprising a correction unit adapted to correct the detecting signals before combining the detecting signals.

8. The computer tomography apparatus according to claim 7, wherein the correction unit is adapted to correct the detecting signals with respect to sensitivity fluctuations and/or with respect to energy scale fluctuations.

9. The computer tomography apparatus according to claim 1, comprising a normalizing unit adapted to normalize the detecting signals before combining the detecting signals.

10. The computer tomography apparatus according to claim 1, comprising an attenuation correction unit adapted to correct influences of attenuation of the detecting signals before combining the detecting signals.

11. The computer tomography apparatus according to claim 1, comprising a determination unit adapted to determine structural information concerning the object of interest based on an analysis of the combined detecting signals.

12. The computer tomography apparatus according to claim 1, further comprising a collimator arranged between the electromagnetic radiation source and the detecting elements, the collimator being adapted to collimate the primary electromagnetic radiation beam emitted by the electromagnetic radiation source.

13. The computer tomography apparatus according to claim 1, being adapted as a coherent scatter computer tomography apparatus.

14. The computer tomography apparatus according to claim 1, wherein the detecting elements form a multi-line detector array.

15. The computer tomography apparatus according to claim 1, wherein the detecting elements form a detector array having a plurality of rows and having a plurality of columns of detecting elements, wherein the combination unit is adapted to combine detecting signals detected by different detecting elements of a column.

16. The computer tomography apparatus according to claim 1, configured as one of the group consisting of a baggage inspection apparatus, a medical application apparatus, a material testing apparatus and a material science analysis apparatus.

17. A method of examining an object of interest with a computer tomography apparatus, the method comprising the acts of:
emitting primary electromagnetic radiation toward the object of interest;
detecting, as detecting signals, electromagnetic radiation scattered from the object of interest in an energy-resolving manner; and
combining different detecting signals such as to reduce the amount of data to be processed for determining structural information concerning the object of interest;
wherein the combining act combines signals with an essentially equal product of energy of the detected electromagnetic radiation and a distance of the detected electromagnetic radiation from the primary electromagnetic radiation detected by a detecting element, including signals having different energies and different distances.

18. A computer readable medium, in which a computer program of examining an object of interest with a computer tomography apparatus is stored which, when being executed by a processor, is adapted to carry out the acts of:
emitting primary electromagnetic radiation toward the object of interest;
detecting, as detecting signals, electromagnetic radiation scattered from the object of interest in an energy-resolving manner; and
combining different detecting signals such as to reduce the amount of data to be processed for determining structural information concerning the object of interest;
wherein the combining act combines signals with an essentially equal product of energy of the detected electromagnetic radiation and a distance of the detected electromagnetic radiation from the primary electromagnetic radiation detected by a detecting element, including signals having different energies and different distances.

19. A computer program stored on a computer readable memory medium, the computer program being configured for examining an object of interest, which, when being executed by a processor, is adapted to carry out the acts of:
detecting, as detecting signals, electromagnetic radiation scattered from an object of interest in an energy-resolving manner; and
combining different detecting signals such as to reduce the amount of data to be processed for determining structural information concerning the object of interest;
wherein the combining act combines signals with an essentially equal product of energy of the detected electromagnetic radiation and a distance of the detected electromagnetic radiation from the primary electromagnetic radiation detected by a detecting element, including signals having different energies and different distances.

* * * * *